US012336893B2

(12) United States Patent
Heege et al.

(10) Patent No.: US 12,336,893 B2
(45) Date of Patent: Jun. 24, 2025

(54) PROCESS AND APPARATUS FOR MAKING CHANNELED ABSORBENT ARTICLES (71) Applicants: ONTEX BV, Buggenhout (BE); ONTEX GROUP NV, Erembodegem (BE)

(72) Inventors: Thomas Heege, Düngenheim (DE); Ainas Weber, Bad Neuenahr-Ahrweiler (DE); Christel Mailinger, Elz (DE); Manfred Breu, Luxem (DE); Detlef Vollrath, Treis-Karden (DE); Alissa Idelson, Rheinbach (DE); Christoph Wagner, Mayen (DE)

(73) Assignees: ONTEX BV, Buggenhout (BE); ONTEX GROUP NV, Erembodegem (BE)

( * ) Notice: Subject to any disclaimer, the term of this patent is extended or adjusted under 35 U.S.C. 154(b) by 0 days.

(21) Appl. No.: 18/896,685

(22) Filed: Sep. 25, 2024

(65) Prior Publication Data
US 2025/0009569 A1 Jan. 9, 2025

Related U.S. Application Data (62) Division of application No. 17/440,828, filed as application No. PCT/EP2020/057824 on Mar. 20, 2020, now Pat. No. 12,127,922.

(30) Foreign Application Priority Data

Mar. 21, 2019 (EP) ..................... 19164452
Dec. 20, 2019 (EP) ..................... 19218948
(Continued)

(51) Int. Cl.
*A61F 13/475* (2006.01)
*A61F 13/15* (2006.01)
(Continued)

(52) U.S. Cl.
CPC .... *A61F 13/4756* (2013.01); *A61F 13/15634* (2013.01); *A61F 13/15658* (2013.01);
(Continued)

(58) Field of Classification Search
CPC ....... B65C 9/1803; B65C 9/18; B65C 9/1819; B65C 9/1815; B65C 9/1807; B65C 2009/1838
See application file for complete search history.

(56) References Cited

U.S. PATENT DOCUMENTS 3,444,732 A  5/1969 Robbins et al.
3,826,701 A  7/1974 Miller
(Continued)

FOREIGN PATENT DOCUMENTS

CN  106999317 A  8/2017
EP  0539703 A1  5/1993
(Continued)

OTHER PUBLICATIONS

Communication Pursuant to Article 94(3) EPC in European App. No. 20158150.1, mailed Sep. 30, 2020.
(Continued)

*Primary Examiner* — George R Koch
*Assistant Examiner* — Christopher C Caillouet
(74) *Attorney, Agent, or Firm* — VIVICAR Law, PLLC (57) ABSTRACT A method for making an absorbent article comprising an absorbent core comprising one or more channels, the method comprising the steps of: i. providing a first endless moving surface comprising a plurality of molds, each mold comprising a non-porous insert therein, typically said insert having the inverse shape of said channel(s), wherein the molds are in fluid communication with an under-pressure source except for said insert; ii. feeding a first nonwoven
(Continued)

web to said first endless moving surface and over one or more said molds; iii. depositing an absorbent material, comprising cellulose fibers and/or superabsorbent polymer particles, over at least a portion of said nonwoven web; iv. removing said absorbent material from areas of the nonwoven web corresponding to said insert; v. applying a second nonwoven web directly or indirectly over the absorbent material, or folding said first nonwoven web, such to sandwich said absorbent material between upper and lower layers of said nonwoven web(s); vi. joining said upper and lower layers together at least in the areas of the nonwoven web(s) corresponding to the insert to form an absorbent core having one or more channels substantially free of absorbent material; vii. optionally joining an acquisition distribution layer to said absorbent core, typically a skin facing surface of said upper layer; viii. optionally laminating said absorbent core and acquisition distribution layer between a liquid pervious topsheet and a liquid impervious backsheet; wherein step vi. comprises the step of selectively applying a first pressure onto the absorbent core, preferably only, in a central portion thereof and a second pressure, preferably only, along peripheral longitudinal side edges thereof running opposite and parallel to each other and being outboard of said central portion, said central portion corresponding at least to a region of the core comprising said channel(s), and wherein said first and second pressures are successively applied along a machine direction (MD).

16 Claims, 7 Drawing Sheets

(30) Foreign Application Priority Data

| | | |
|---|---|---|
| Feb. 11, 2020 | (BE) | 2020/0018 |
| Feb. 19, 2020 | (EP) | 20158150 |
| Mar. 19, 2020 | (EP) | 20164374 |
| Mar. 19, 2020 | (WO) | PCT/EP2020/057659 |
| Mar. 19, 2020 | (WO) | PCT/EP2020/057684 |

(51) Int. Cl.
| | |
|---|---|
| *A61F 13/42* | (2006.01) |
| *A61F 13/533* | (2006.01) |
| *A61F 13/536* | (2006.01) |
| *A61L 15/28* | (2006.01) |
| *A61L 15/42* | (2006.01) |
| *A61L 15/60* | (2006.01) |
| *D04H 1/4291* | (2012.01) |
| *D04H 1/54* | (2012.01) |
| *D04H 3/007* | (2012.01) |
| *D04H 3/14* | (2012.01) |
| *A61F 13/531* | (2006.01) |

(52) U.S. Cl.
CPC ........ *A61F 13/15707* (2013.01); *A61F 13/42* (2013.01); *A61F 13/533* (2013.01); *A61F 13/536* (2013.01); *A61L 15/28* (2013.01); *A61L 15/425* (2013.01); *A61L 15/60* (2013.01); *D04H 1/4291* (2013.01); *D04H 1/54* (2013.01); *D04H 3/007* (2013.01); *D04H 3/14* (2013.01); *A61F 2013/15821* (2013.01); *A61F 2013/5312* (2013.01)

(56) References Cited

U.S. PATENT DOCUMENTS

| | | | |
|---|---|---|---|
| 3,925,139 | A | 12/1975 | Simmons |
| 5,376,198 | A | 12/1994 | Fahrenkrug et al. |
| 5,433,715 | A | 7/1995 | Tanzer et al. |
| 5,486,166 | A | 1/1996 | Bishop et al. |
| 5,520,673 | A | 5/1996 | Yarbrough et al. |
| 5,700,254 | A | 12/1997 | McDowall et al. |
| 5,756,039 | A | 5/1998 | McFall et al. |
| 6,503,233 | B1 | 1/2003 | Chen et al. |
| 7,786,341 | B2 | 8/2010 | Schneider et al. |
| 2005/0008839 | A1 | 1/2005 | Cramer et al. |
| 2006/0095012 | A1 | 5/2006 | Cohen |
| 2006/0184150 | A1 | 8/2006 | Noel |
| 2007/0246147 | A1 | 10/2007 | Venturino et al. |
| 2009/0270825 | A1 | 10/2009 | Wciorka et al. |
| 2012/0312491 | A1 | 12/2012 | Jackels et al. |
| 2012/0316528 | A1 | 12/2012 | Kreuzer et al. |
| 2014/0163500 | A1 | 6/2014 | Roe et al. |
| 2014/0163506 | A1 | 6/2014 | Roe et al. |
| 2015/0088084 | A1 | 3/2015 | Baker et al. |
| 2015/0290047 | A1 | 10/2015 | Royce et al. |
| 2016/0074243 | A1 | 3/2016 | Rosati et al. |
| 2016/0206482 | A1 | 7/2016 | Nishikawa et al. |
| 2017/0065465 | A1 | 3/2017 | Rosati et al. |
| 2017/0079858 | A1 | 3/2017 | Willhaus et al. |
| 2018/0161217 | A1 | 6/2018 | Roe et al. |
| 2019/0000687 | A1 | 1/2019 | Bianchi et al. |

FOREIGN PATENT DOCUMENTS

| | | |
|---|---|---|
| EP | 1077052 A1 | 2/2001 |
| EP | 1078617 A2 | 2/2001 |
| EP | 1088536 A2 | 4/2001 |
| EP | 1267775 B1 | 9/2004 |
| EP | 1621167 A2 | 2/2006 |
| EP | 1349524 B1 | 1/2010 |
| EP | 2211808 B1 | 10/2012 |
| EP | 2532329 A1 | 12/2012 |
| EP | 1959903 B1 | 2/2014 |
| EP | 2905000 A1 | 8/2015 |
| EP | 2905001 A1 | 8/2015 |
| EP | 3190216 A1 | 7/2017 |
| EP | 3238676 A1 | 11/2017 |
| EP | 3315106 A1 | 5/2018 |
| EP | 3342386 A1 | 7/2018 |
| EP | 3403630 A1 | 11/2018 |
| EP | 3711729 A1 | 9/2020 |
| EP | 3560469 B1 | 6/2021 |
| WO | 9706765 A1 | 2/1997 |
| WO | 0066058 A1 | 11/2000 |
| WO | 2012170778 A1 | 12/2012 |
| WO | 2013056978 A2 | 4/2013 |
| WO | 2015084221 A1 | 6/2015 |
| WO | 2016114947 A1 | 7/2016 |
| WO | 2018122234 A1 | 7/2018 |

OTHER PUBLICATIONS

International Search Report and Written Opinion for PCT/EP2020/057824, mailed Jun. 30, 2020.

PROCESS AND APPARATUS FOR MAKING CHANNELED ABSORBENT ARTICLES

CROSS-REFERENCE TO RELATED APPLICATIONS

This application is a divisional of U.S. application Ser. No. 17/440,828, filing date Sep. 20, 2021, which is the national stage application of corresponding international application number PCT/EP2020/057824, filed Mar. 20, 2020, which claims priority to and the benefit of European application no. 19164452.5, filed Mar. 21, 2019, European application no. 19218948.8, filed Dec. 20, 2019, European application no. 20164374.9, filed Mar. 19, 2020, Belgian application no. BE2020/0018, filed Feb. 11, 2020, international application no. PCT/EP2020/057659, filed Mar. 19, 2020, international application no. PCT/EP2020/057684, filed Mar. 19, 2020, and European application no. 20158150.1, filed Feb. 19, 2020, which are hereby incorporated by reference in their entireties.

TECHNICAL FIELD

The disclosure pertains to the technical field of absorbent hygiene products and methods of making thereof. In particular, the present disclosure relates to apparatus and methods of making absorbent systems comprising an absorbent core and further distribution layers (such as acquisition distribution layers and/or core wrap layers typically having additional functional characteristics of said acquisition distribution layers) that can be used within an article for absorbing body fluids and exudates, such as urine and fecal material, or blood, menses, and vaginal fluids. More particularly, the present disclosure relates to absorbent garments (or articles), such as disposable diapers or diaper pants, disposable incontinence diapers or pants, and which are configured to collect and contain fecal material and avoid leakage, or sanitary napkins or panty liners, which are configured to collect and contain blood, menses, urine, vaginal fluids and avoid leakage.

BACKGROUND

The disclosure relates to apparatus and process of making an absorbent core for an absorbent article, in particular for hygiene articles, to absorbent articles comprising said absorbent core and to processes for providing said absorbent core. In particular to cores having one or more channels therethrough.

Absorbent cores have been subject to considerable improvement and innovation over time to address needs such as improved fluid absorption and distribution, as well as comfort, and a need for continued improvement exists. Such needs are ever present in today's demanding consumer environment. The following paragraphs elucidate on some of the relevant disclosures pertaining to this subject.

EP 1077052 A1 and EP 1078617 A2 disclose a sanitary napkin allowing controlled deformation in response to lateral compression when in use. The sanitary napkin has preferential bending zones extending along a longitudinal axis formed by a process of perforating, slitting, cutting or embossing.

EP 1959903 B1 discloses an incontinence pad comprising a pair of folding lines dividing the absorbent core material into a central portion and a pair of longitudinal side portions to adapt better to the body of the user. The folding lines are formed by compression of the absorbent material.

EP 2211808 B1 discloses an absorbent core comprising an upper absorbent core and a lower absorbent core. The upper absorbent core comprises fold indications enabling the absorbent core to adopt a predetermined three-dimensional shape when subjected to pressure in the width direction. The fold indications are cuts or compression lines which do or do not extend completely through the upper core.

EP 1349524 B1 discloses a pantiliner comprising at least one fold line defining a central area and two side areas which allows adjusting the size of the pantiliner by folding the pantiliner along the fold line. The fold lines are lines of embossing.

EP 1267775 B1 discloses a sanitary pad that conforms to the body confinements. The sanitary pad comprises a forward wide portion and a rear narrow portion and at least two fold lines preformed on the upper or lower surface of the narrow portion. The fold lines may be selected from mechanically pressed lines, chemically joined constituents forming the lines, heat generated lines, laser generated lines, adhesive generated lines and/or mechanical vibration generated lines.

EP1088536 A2 discloses a hygiene napkin provided with corrugations making it possible to adapt the hygienic napkin to the user's panties.

U.S. Pat. No. 5,756,039 A discloses an absorbent core comprising distinct segments which can be independently displaced by a lifting member. The lifting member ensures that the top sheet conforms to the wearer's body.

US 2006/0184150 A1 discloses an absorbent core with varying flexibility that act as shaping element for improved body fit. The absorbent core can have lines of reduced bending resistance which are formed by removal of material, e.g. in the form of apertures or slots.

U.S. Pat. No. 6,503,233 B1 discloses an absorbent article comprising a combination of downwardly-deflecting crease lines and an upward-deflecting shaping line to achieve a geometry for improved body fit. The crease lines are formed by embossing of the absorbent material. The shaping line is formed by perforation or notching.

US 2015/0088084 A1, discloses a method of making an absorbent structure having a three-dimensional topography including placing at least a portion of the absorbent structure between opposed mold surfaces. At least one of the mold surfaces has a three-dimensional topography. The three-dimensional topography of the mold surface is imparted onto the absorbent structure so that the absorbent structure has a three-dimensional topography corresponding to the three-dimensional topography of the mold surface.

EP3342386A1, discloses an absorbent core comprising substantially continuous zones of one or more high fluid distribution structures and discontinuous zones of fluid absorption structures surrounding the one or more high fluid distribution structures, wherein the one or more high fluid distribution structures are arranged to distribute fluid across the absorbent core at a speed that is faster than the speed of fluid distribution across the absorbent core by said discontinuous fluid absorption structures, and wherein said continuous zones extend along a path that is substantially parallel to at least a portion of the perimeter of the core, said portion of the perimeter of the core comprising at least a portion of the sides of the core and one of the ends of the core.

Apparatuses and processes of making such cores are described in EP3342386A1 and comprise the use of a 3D insert having the inverse shape of the desired channels in combination with a vacuum source. It is nevertheless desirable to improve adhesion between top and bottom layers of the core wrap forming the absorbent material free channels.

EP2905001A1, discloses an apparatus and method for making an absorbent structure for an absorbent article, comprising a supporting sheet and thereon an absorbent layer, the absorbent layer comprising an absorbent material. According to the disclosure a first moving endless surface is provided which has one or more substantially longitudinally extending first mating strips, and at least one further auxiliary moving endless with second mating strips on its surface is provided which act against the first mating strips. Pressure is applied between the first and second mating strips and to the first and second supporting sheets at least within a part of the area of the channels, so as to adhere together the first and second supporting sheets. Such mating strip arrangement requires locating the further auxiliary moving endless surface to act directly onto the first moving endless surface in order to avoid the need for a registered process.

A need nevertheless exists for improving adhesion of core wrap sheets in absorbent cores comprising channels that allow for improved process flexibility and that limits wear and tear of respective apparatus components especially at high production speeds for extended continuous periods of time.

SUMMARY

In a first aspect, the disclosure relates to a method for making an absorbent article comprising an absorbent core comprising one or more channels, the method comprising the steps of: i. providing a first endless moving surface comprising a plurality of molds, each mold comprising a non-porous insert therein, typically said insert having the inverse shape of said channel(s), wherein the molds are in fluid communication with an under-pressure source except for said insert; ii. feeding a first nonwoven web to said first endless moving surface and over one or more said molds; iii. depositing an absorbent material, comprising cellulose fibers and/or superabsorbent polymer particles, over at least a portion of said nonwoven web; iv. removing said absorbent material from areas of the nonwoven web corresponding to said insert; v. applying a second nonwoven web directly or indirectly over the absorbent material, or folding said first nonwoven web, such to sandwich said absorbent material between upper and lower layers of said nonwoven web(s); vi. joining said upper and lower layers together at least in the areas of the nonwoven web(s) corresponding to the insert to form an absorbent core having one or more channels substantially free of absorbent material; vii. optionally joining an acquisition distribution layer to said absorbent core, typically a skin facing surface of said upper layer; viii. optionally laminating said absorbent core and acquisition distribution layer between a liquid pervious topsheet and a liquid impervious backsheet; wherein step vi. comprises the step of selectively applying a first pressure onto the absorbent core, preferably only, in a central portion thereof and a second pressure, preferably only, along peripheral longitudinal side edges thereof running opposite and parallel to each other and being outboard of said central portion, said central portion corresponding at least to a region of the core comprising said channel(s), and wherein said first and second pressures are successively applied along a machine direction (MD).

In a second aspect, the disclosure relates to a method for making an absorbent article comprising an absorbent core comprising one or more channels, the method comprising the steps of: i. providing a first endless moving surface comprising a plurality of molds, each mold comprising a non-porous insert therein, typically said insert having the inverse shape of said channel(s), wherein the molds are in fluid communication with an under-pressure source except for said insert; ii. feeding a first nonwoven web to said first endless moving surface and over one or more said molds; iii. depositing an absorbent material, comprising cellulose fibers and/or superabsorbent polymer particles, over at least a portion of said nonwoven web; iv. removing said absorbent material from areas of the nonwoven web corresponding to said insert; v. applying a second nonwoven web directly or indirectly over the absorbent material, or folding said first nonwoven web, such to sandwich said absorbent material between upper and lower layers of said nonwoven web(s); vi. joining said upper and lower layers together at least in the areas of the nonwoven web(s) corresponding to the insert to form an absorbent core having one or more channels substantially free of absorbent material; vii. optionally joining an acquisition distribution layer to said absorbent core, typically a skin facing surface of said upper layer; viii. optionally laminating said absorbent core and acquisition distribution layer between a liquid pervious topsheet and a liquid impervious backsheet; wherein step vi. comprises the step of selectively applying a first pressure onto the absorbent core, preferably only, in a central portion thereof and a further pressure onto the absorbent core, preferably only, in the central portion thereof, wherein said further pressure is applied upstream of said first pressure and arranged to provide a pre-compression force onto the absorbent core in an area of said core corresponding to said channels.

In a third aspect, the disclosure relates to an apparatus for making an absorbent article comprising an absorbent core comprising one or more channels, said apparatus comprising: a first endless moving surface in the form of a rotating drum, said drum comprising a plurality of molds in the form of pockets successively positioned along a circumference of said drum, wherein each mold comprises a non-porous insert therein, said insert preferably having the inverse shape of said channel(s), wherein the molds are in fluid communication with an under-pressure source except for said insert such to form one or more non-suction zones corresponding to said non-porous insert and a suction zone surrounding said non-porous insert; a first feeding unit for feeding a first nonwoven web to said first endless moving surface and over one or more said molds; a first adhesive application unit for applying an adhesive pattern over a skin-facing surface of said first nonwoven web; an absorbent material deposition unit for depositing an absorbent material, typically comprising cellulose fibers and/or superabsorbent polymer particles, over at least a portion of said first nonwoven web; a second feeding unit for feeding a second nonwoven web directly or indirectly over the absorbent material such to sandwich said absorbent material between upper and lower layers of said nonwoven webs to form an absorbent core; or a folding unit for folding said first nonwoven web such to sandwich said absorbent material between upper and lower layers of said nonwoven web to form an absorbent core; optionally a second adhesive application unit for applying an adhesive pattern over a garment-facing surface of said second nonwoven web positioned upstream a joining position of said second nonwoven web to said first nonwoven web; optionally a removing unit for removing said absorbent material from areas of the nonwoven web corresponding to said insert such that at least one portion of the nonwoven web located above the suction zone is covered with absorbent material and substantially no absorbent material is present on portions corresponding to the non-suction zone; a first auxiliary endless moving surface for applying a first pressure to the upper and lower layers of said nonwoven web(s); wherein the apparatus further comprises a second and third auxiliary endless moving surfaces for applying a second pressure to the upper and lower layers of said nonwoven web(s), wherein said first endless moving surface, said first auxiliary endless moving surface, said second auxiliary endless moving surface and said third auxiliary endless moving surface each have an axis of rotation being substantially parallel to each other, and wherein the first endless moving surface and the auxiliary endless moving surfaces act upon each other by applying pressure to the upper and lower layers of said nonwoven web(s), and wherein said first auxiliary endless moving surface is arranged to selectively apply said first pressure onto the absorbent core, preferably only, in a central portion thereof and said second and third auxiliary endless moving surfaces are arranged to selectively apply said second pressure, preferably only, along peripheral longitudinal side edges of said absorbent core running opposite and parallel to each other and being outboard of said central portion, said central portion corresponding at least to a region of the core comprising said channel(s).

In a further aspect, the disclosure relates to the use of an apparatus, according to the above and disclosed embodiments herein, in making an absorbent article comprising an absorbent core comprising one or more channels, wherein top and bottom layers of the nonwoven web(s) are joined together in an area corresponding to the channel(s) and, preferably sequentially thereafter, in areas corresponding to the peripheral longitudinal side edges of said absorbent core running opposite and parallel to each other and being outboard of the central portion of the absorbent core comprising the channel(s), for increasing production speed and/or avoiding process registration

DETAILED DESCRIPTION

Unless otherwise defined, all terms used in disclosing characteristics of the disclosure, including technical and scientific terms, have the meaning as commonly understood by one of ordinary skill in the art to which this disclosure belongs. By means of further guidance, term definitions are included to better appreciate the teaching of the present disclosure.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed disclosure. However, it is to be understood that the value to which the modifier "about" refers is itself also specifically disclosed.

"Comprise", "comprising", and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The expression "% by weight" (weight percent), here and throughout the description unless otherwise defined, refers to the relative weight of the respective component based on the overall weight of the formulation.

The recitation of numerical ranges by endpoints includes all numbers and fractions subsumed within that range, as well as the recited endpoints unless otherwise stated.

"Absorbent article" refers to devices that absorb and contain liquid, and more specifically, refers to devices that are placed against or in proximity to the body of the wearer to absorb and contain the various exudates discharged from the body. Absorbent articles include but are not limited to diapers, adult incontinence briefs, training pants, diaper holders and liners, sanitary napkins and the like, as well as surgical bandages and sponges. Absorbent articles preferably comprise a longitudinal axis and a transversal axis perpendicular to said longitudinal axis. The longitudinal axis is hereby conventionally chosen in the front-to-back direction of the article when referring to the article being worn, and the transversal axis is conventionally chosen in the left-to-right direction of the article when referring to the article being worn. Disposable absorbent articles can include a liquid pervious top sheet, a back sheet joined to the top sheet, and an absorbent core positioned and held between the top sheet and the back sheet. The top sheet is operatively permeable to the liquids that are intended to be held or stored by the absorbent article, and the back sheet may or may not be substantially impervious or otherwise operatively impermeable to the intended liquids. The absorbent article may also include other components, such as liquid wicking layers, liquid intake layers, liquid distribution layers, transfer layers, barrier layers, wrapping layers and the like, as well as combinations thereof. Disposable absorbent articles and the components thereof can operate to provide a body-facing surface and a garment-facing surface.

An absorbent article, such as a diaper, comprises a front waistband region, a back waistband region, an intermediate crotch region which interconnects the front and rear waistband regions. When used herein, reference to a "front" portion refers to that part of the absorbent article which is generally located on the front of a subject, such as an infant or adult, when in use. Reference to the "rear" portion refers to the portion of the absorbent article generally located at the rear of the subject, such as an infant or adult, when in use, and reference to the "crotch" portion refers to that portion which is generally located between the legs of subject, such as an infant or adult, when in use. The crotch region is an area where repeated fluid surge typically occurs, within the absorbent article assembly.

"Mechanical bond" is an attachment between two or more elements, components, regions, or webs and may comprise heat bonds, pressure bonds, ultrasonic bonds, dynamic mechanical bonds, or any other suitable non-adhesive attachment means or combinations of these attachment means as are known in the art.

"Acquisition and distribution layer", "ADL" or "surge management portion" refers to a sub-layer which preferably is a nonwoven wicking layer under the top sheet of an absorbent product, which speeds up the transport and improves distribution of fluids throughout the absorbent core. The surge management portion is typically less hydrophilic than the retention portion, and has the ability to quickly collect and temporarily hold liquid surges, and to transport the liquid from its initial entrance point to other parts of the absorbent structure, particularly the retention portion. This configuration can help prevent the liquid from pooling and collecting on the portion of the absorbent garment positioned against the wearer's skin, thereby reducing the feeling of wetness by the wearer. Preferably, the surge management portion is positioned between the top sheet and the retention portion.

The term "adhesive" as used herein is intended to refer to any suitable hot melt, water or solvent borne adhesive that can be applied to a surface of a film layer in the required pattern or network of adhesive areas to form the film-nonwoven laminate of the present disclosure. Accordingly, suitable adhesives include conventional hot melt adhesives, pressure-sensitive adhesives and reactive adhesives (i.e., polyurethane).

As used herein, the "skin facing", "body-facing" or "bodyside" surface means that surface of the article or component which is intended to be disposed toward or placed adjacent to the body of the wearer during ordinary use, while the "outward", "outward-facing" or "garment-side" surface is on the opposite side, and is intended to be disposed to face away from the wearer's body during ordinary use. Such outward surface may be arranged to face toward or placed adjacent to the wearer's undergarments when the absorbent article is worn.

"Bonded" refers to the joining, adhering, connecting, attaching, or the like, of at least two elements. Two elements will be considered to be bonded together when they are bonded directly to one another or indirectly to one another, such as when each is directly bonded to intermediate elements.

The term "consisting essentially of" does not exclude the presence of additional materials which do not significantly affect the desired characteristics of a given composition or product. Exemplary materials of this sort would include, without limitation, pigments, antioxidants, stabilizers, surfactants, waxes, flow promoters, solvents, particulates and materials added to enhance processability of the composition.

The term "disposable" is used herein to describe absorbent articles that generally are not intended to be laundered or otherwise restored or reused as an absorbent article (i.e., they are intended to be discarded after a single use and, preferably, to be recycled, composted or otherwise disposed of in an environmentally compatible manner).

As used herein, the terms "elastic", "elastomeric", "elasticity" or derivations thereof are used to describe the ability of various materials and objects comprised of such to reversibly undergo deformation under stress, e.g., become stretched or extended, in at least one direction when a force is applied to the material and to resume substantially to their original dimensions upon relaxing, i.e., when the force is released, without rupture or breakage. Preferably, it refers to a material or composite which can be elongated in at least one direction by at least 50% of its relaxed length, i.e., elongated to at least 150% of its relaxed length, and which will recover upon release of the applied tension at least 40% of its elongation. Accordingly, upon release of the applied tension at 50% elongation, the material or composite contracts to a relaxed length of not more than 130% of its original length. Examples of suitable elastomer materials include polyether-polyamide block copolymers, polyurethanes, synthetic linear A-B-A and A-B block copolymers, chlorinated rubber/EVA (ethylene-vinyl acetate) blends, EPDM (ethylene-propylene diene monomer) rubbers, EPM (ethylene-propylene monomer) rubbers, blends of EPDM/EPM/EVA, and the like.

As used herein, the term "garment" means any type of apparel which may be worn. This includes diapers, training pants, incontinence products, surgical gowns, industrial workwear and coveralls, undergarments, pants, shirts, jackets and the like.

"Join", "joining", "joined", or variations thereof, when used in describing the relationship between two or more elements, means that the elements can be connected together in any suitable manner, such as by heat sealing, ultrasonic bonding, thermal bonding, by adhesives, stitching, or the like. Further, the elements can be joined directly together, or may have one or more elements interposed between them, all of which are connected together.

By "channels", it is meant that the structure referred to (e.g. the absorbent core) comprises recessed regions forming visible conduits or passages typically extending along the longitudinal axis of the core and having a depth in a direction perpendicular to said longitudinal axis. By "visible" it is herein intended clearly visible by naked eye and typically that the channels have a width generally greater than 1 mm, preferably from 5 mm to 50 mm, more preferably from 8 mm to 40 mm, more preferably from 10 mm to 30 mm, even more preferably from greater than 10 mm to less than 25 mm.

By "interconnected", it is meant that the structure referred to (e.g. the channels) from a substantially continuous path such as from a first end of a channel to a second end of the same channel.

By "substantially", it is meant at least the majority of the structure referred to. For example, with reference to interconnected channels, "substantially interconnected" means that the majority of the channel is interconnected and generally wherein a direct and continuous path can be traced by starting from one end of the channel towards another end of the channel, said ends (also referred to herein as terminal positions) may be distal to each other in a width direction of the core and proximal to a portion of the perimeter of the core, preferably the sides thereof.

By "directly over", it is meant that the feature referred to is placed over the structure referred to such that the two are in direct contact with each other at least throughout a substantial portion of said structure.

By "indirectly over", it is meant that the feature referred to is placed over the structure referred to but in such a way that the two are not in direct contact with each other at least throughout a substantial portion of said structure. For example, a nonwoven web applied indirectly over a three-dimensional absorbent material comprises a further layer of material between said nonwoven web and said three-dimensional absorbent material.

"Superabsorbent polymer particles" or "SAPs" refer to water-swellable, water-insoluble organic or inorganic materials capable, under the most favorable conditions, of absorbing at least about 10 times their weight, or at least about 15 times their weight, or at least about 25 times their weight in an aqueous solution containing 0.9 weight percent sodium chloride. In absorbent articles, such as diapers, incontinent diapers, etc., the particle size is typically ranging between 100 to 800 μm, preferably between 300 to 600 μm, more preferably between 400 to 500 μm.

Embodiments of the articles and processes according to the disclosure will now be described. It is understood that technical features described in one or more embodiments maybe combined with one or more other embodiments without departing from the intention of the disclosure and without generalization therefrom.

THE APPARATUS

Figure 1:
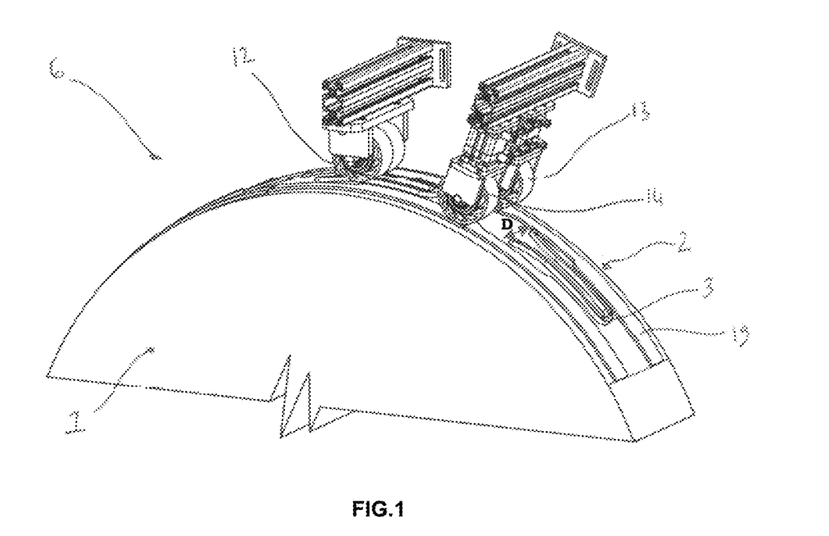
FIG. 1 shows a perspective view of a portion of an apparatus according to an embodiment herein.
Figure 2:
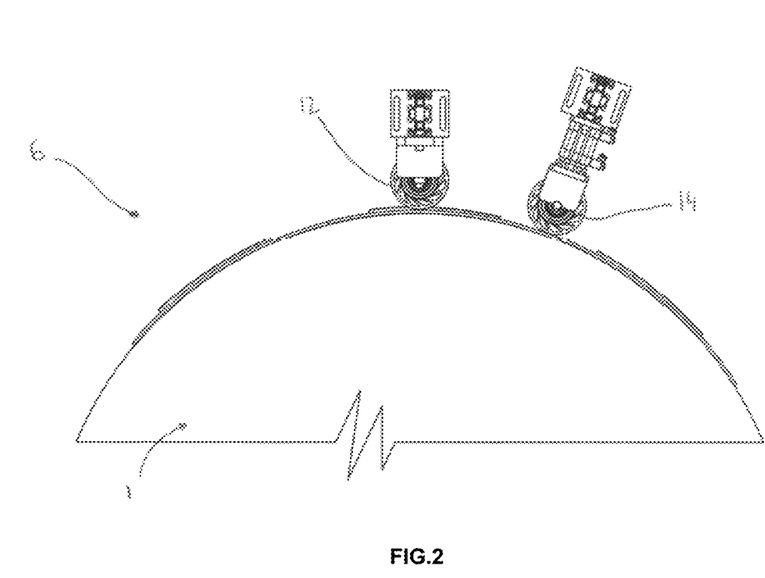
FIG. 2 shows a side view of the apparatus of FIG. 1.

As exemplified in FIG. 1-2, the apparatus (6) for making an absorbent article (as used herein absorbent articles typically being disposable) comprising an absorbent core comprising one or more channels, said apparatus comprises: a first endless moving surface (1) in the form of a rotating drum, said drum comprising a plurality of molds (2) in the form of pockets successively positioned along a circumference of said drum, wherein each mold (2) comprises a non-porous insert (3) therein, said insert (3) preferably having the inverse shape of said channel(s), wherein the molds (2) are in fluid communication with an under-pressure source except for said insert (3) such to form one or more non-suction zones corresponding to said non-porous insert (3) and a suction zone surrounding said non-porous insert (3); a first feeding unit (7) for feeding a first nonwoven web (4) to said first endless moving surface (1) and over one or more said molds (2); a first adhesive application unit (8) for applying an adhesive pattern over a skin-facing surface of said first nonwoven web (4); an absorbent material deposition unit (9) for depositing an absorbent material, typically comprising cellulose fibers and/or superabsorbent polymer particles, over at least a portion of said first nonwoven web (4); a second feeding unit for feeding a second nonwoven web (5) directly or indirectly over the absorbent material such to sandwich said absorbent material between upper and lower layers of said nonwoven webs (4, 5) to form an absorbent core; or a folding unit for folding said first nonwoven web (4) such to sandwich said absorbent material between upper and lower layers of said nonwoven web (4) to form an absorbent core; optionally a second adhesive application unit (10) for applying an adhesive pattern over a garment-facing surface of said second nonwoven web (5) positioned upstream a joining position of said second nonwoven web (5) to said first nonwoven web (4); optionally a removing unit (11) for removing said absorbent material from areas of the nonwoven web (4) corresponding to said insert (3) such that at least one portion of the nonwoven web (4) located above the suction zone is covered with absorbent material and substantially no absorbent material is present on portions corresponding to the non-suction zone; a first auxiliary endless moving surface (12) for applying a first pressure to the upper and lower layers of said nonwoven web(s) (4, 5); wherein the apparatus (6) further comprises a second and third auxiliary endless moving surfaces for applying a second pressure to the upper and lower layers of said nonwoven web(s) (4, 5), wherein said first endless moving surface (1), said first auxiliary endless moving surface (12), said second auxiliary endless moving surface (13) and said third auxiliary endless moving surface (14) each have an axis of rotation being substantially parallel to each other, and wherein the first endless moving surface (1) and the auxiliary endless moving surfaces (12, 13, 14) act upon each other by applying pressure to the upper and lower layers of said nonwoven web(s) (4, 5), and wherein said first auxiliary endless moving surface (12) is arranged to selectively apply said first pressure onto the absorbent core, preferably only, in a central portion thereof and said second and third auxiliary endless moving surfaces (13, 14) are arranged to selectively apply said second pressure, preferably only, along peripheral longitudinal side edges of said absorbent core running opposite and parallel to each other and being outboard of said central portion, said central portion corresponding at least to a region of the core comprising said channel(s). Advantageously, such selective application of pressure on the central part of the core and separately on the peripheral longitudinally extending edges (i.e. extending parallel to the machine direction MD) of the core allows for appropriate joining of the core wrap layers where its needed without the need of profiled pressure rollers and thus allowing to avoid the use of a registered process and further to limit wear and tear of components and thus run at faster production speeds, all this with limited risk of damaging the core wrap layers by avoiding over-compression of the absorbent material in regions of the core where the top and bottom core wrap layers are not to be joined.

In an embodiment, the removing unit (11) is in the form of a rotating brush that comprises a plurality of bristles. Alternatively, a static brush may be used or other means such as blowing of air that are suitable to remove any excess absorbent material that may deposit on the nonwoven web corresponding to the channel or insert (3) (i.e. the non-suction zone).

In an embodiment, the insert (3) has a thickness t along an axis perpendicular to both the axis of rotation of the first endless moving surface (1) and the machine direction (MD), and the mold has a depth d along an axis perpendicular to both the axis of rotation of the first endless moving surface (1) and the machine direction (MD), wherein said thickness t is greater than said depth d such that said insert protrudes outwardly from an apex of said mold (2).

Figure 7:
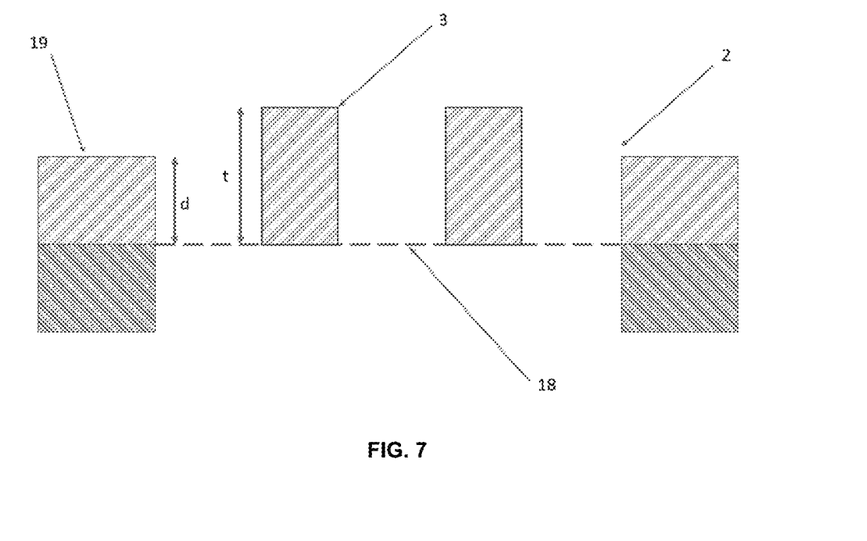
FIG. 7 is a schematic cross-section of pockets comprising an insert according to an embodiment herein.

As illustrated in FIG. 7, pockets (2) herein have a perforated base (18), in fluid communication with the underpressure source generating a vacuum force, longitudinal peripheral edges (19), and the non-porous insert (3) that protrudes beyond the longitudinal peripheral edges to form a non-suction zone corresponding to the position where the top and bottom layers of the core wrap are joined to form absorbent material free channels. The insert (3) may be releasably joined to the base (18) of each pocket (2) via one or more screws, alternative joining means may also be used as long as the insert is releasably for quick interchangeability and change over as may be needed.

In a preferred embodiment, the insert (3) is substantially U-shaped, this is useful for forming absorbent cores that comprise a single interconnected channel (substantially in the form of a U-shape) extending along both a longitudinal (corresponding to an axis substantially parallel to the machine direction MD) and transverse axis (corresponding to an axis substantially parallel to the axis of rotation of the first endless moving surface, such as the drum core former, and perpendicular to the machine direction MD) of said core. Although, this arrangement is preferred, it will be apparent to a person skilled in the art that other channel geometries may equally be attained by changing the shape of the insert. For example interconnected shapes such as substantially V-shaped, X-shaped, Ω-shaped, α-shaped, π-shaped, T-shaped, I-shaped, Y-shaped, etc. are equally contemplated herein. The interconnected channel may also be a single substantially I-shaped channel extending along the centerline of the absorbent core and in this case the insert may be I-shaped and positioned to coincide with the centerline of the pocket extending along the machine direction MD. Moreover, a plurality of channels (whether straight or curved) are also contemplated, for example by replacing the single interconnected insert per pocket with a plurality of inserts for each pocket wherein each insert has the shape of the desired channels that may be symmetrically disposed on each side of a centerline of the pocket extending along the machine direction MD.

In an embodiment, the auxiliary moving surfaces herein are endless, such as in the form of rollers as will be explained in more detail herein below.

In an embodiment, the axis of rotation of the first auxiliary endless moving surface (12) is positioned at a first distance from the axis of rotation of the first endless moving surface (1) and the second and third auxiliary moving surfaces (13, 14) are positioned at a second distance from the axis of rotation of the first endless moving surface (1), and wherein said first distance is greater than said second distance. Advantageously, this allows to apply the correct pressure for joining the longitudinal peripheral edges and central portion of the core whilst limiting risk of damaging the core wrap layers or crushing the superabsorbent polymer particles. Indeed, the peripheral edges of the core are free of absorbent material and typically extend along a circumferential distance that is closer to the axis of rotation of the first endless moving surface compared to the channel regions that sit over the insert as will be described in more detail below, and thus such arrangement ensures not to apply unwanted high pressure on the central portion of the core in areas other than the channel area to bond the top and bottom core wrap layers together in said region.

In an embodiment, the second and third auxiliary moving surfaces (13, 14) are positioned downstream of the first auxiliary moving surface (12) along a machine direction (MD). It is desirable that the first auxiliary endless moving surface (12) is closest possible to the marriage point of the top and bottom core wrap layers in order to ensure a good bond when joining the respective layers together in the channel regions. This ensures limited contamination of the channel by absorbent material and helps to maintain absorbent free channels through the joining step of the process.

Preferably, the second and third auxiliary moving surfaces (13,14) are spaced apart at a distance extending parallel to the axis of rotation thereof, preferably wherein the axis of rotation of said second and third auxiliary surfaces (13, 14) substantially coincide, more preferably wherein the second and third auxiliary moving surfaces (13, 14) are rotatably connected by a common housing. Advantageously, this arrangement allows to apply pressure in the peripheral longitudinal areas of the core only, and thus avoid pressing on other regions of the core that comprise absorbent material, such as the central region thereof.

Figure 3:
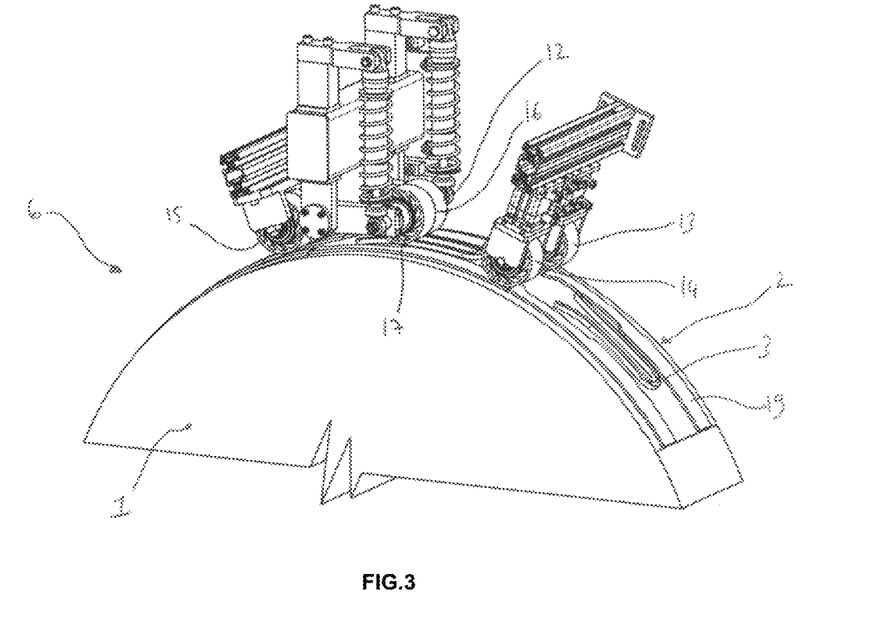
FIG. 3 shows a perspective view of a portion of an apparatus according to an embodiment herein.
Figure 4:
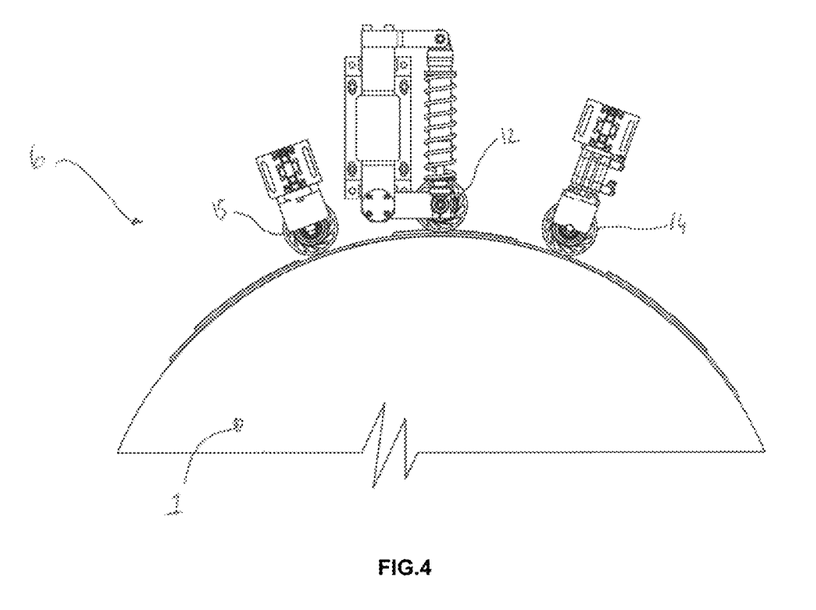
FIG. 4 shows a side view of the apparatus of FIG. 3.

Preferably, as illustrated in FIG. 3-4, the apparatus comprises a fourth auxiliary moving surface (15) arranged to provide a third pressure onto the absorbent core, preferably only, in the central portion thereof, wherein said third pressure is applied upstream of said first pressure, preferably said third pressure arranged to provide a pre-compression force onto the absorbent core, and more preferably wherein the third pressure is less than the first pressure, preferably such that the pre-compression force is less than a force generated by the first pressure onto said absorbent core. It has been found that applying a pre-compression step prior to the final pressure by the first auxiliary endless surface, allows to achieve a stronger bonding force between top and bottom core wrap layers in the channel region whilst at the same time allowing to use individually lower pressures that are beneficial to avoiding undesirable damage to the neighboring areas thereof comprising absorbent material.

Preferably, the second pressure is greater or equal to the first pressure. Alternatively the second pressure is less than or equal to the first pressure.

In an embodiment, the first, second, third, and/or fourth auxiliary moving surfaces (12, 13, 14, 15) comprise an outer surface (also referred to herein as "abrading surface") being made of a substantially pliable material typically selected from the group consisting of plastic, rubber, and silicone, preferably pliable material comprising polyurethane, more preferably elastic polyurethane.

In a preferred embodiment, the first, second, third, and/or fourth auxiliary moving surfaces (12, 13, 14, 15) comprise a substantially smooth outer surface typically free of protruding embossing and/or mating members, said outer surface being made of a substantially pliable material typically selected from the group consisting of plastic, rubber, and silicone, preferably pliable material comprising polyurethane, more preferably elastic polyurethane. Advantageously, this improves the fatigue resistance and allows for higher production speeds to be run without the need for registration.

In an embodiment the first, second, third, and/or fourth auxiliary moving surfaces (12, 13, 14, 15) are made of a material comprising polyurethane and having a Shore A hardness at 85° C. of from 55 to 95, measured according to standard DIN 53505.

In an embodiment the first, second, third, and/or fourth auxiliary moving surfaces (12, 13, 14, 15) are made of a material comprising polyurethane and having a tensile strength of from 9 to 55 MPa, as measured according to standard DIN 53504. Advantageously this contributes to allowing to omit the use of further springs and/or dampeners.

Preferably, the first, second, third, and/or fourth auxiliary moving surfaces (12, 13, 14, 15) each comprise, preferably consist of, rotating pressure rollers.

In a preferred embodiment, the first auxiliary moving surface (12) has a width, extending perpendicular to the machine direction and parallel to the axis of rotation thereof, that is greater than the width of each of the second and third auxiliary moving surfaces (13, 14), and preferably wherein the fourth auxiliary moving surface (15) has a width, extending perpendicular to the machine direction and parallel to the axis of rotation, that is greater or equal to the width of the first auxiliary moving surface (12).

In an embodiment the width of the first auxiliary moving surface (12), and/or fourth auxiliary moving surface (15), is at least equal to a largest distance D between insert portions taken along an axis perpendicular to the machine direction and parallel to the axis of rotation (i.e. perpendicular to the longitudinal peripheral edges (19) of the pockets (2)). It is apparent that although FIG. 1 illustrates the largest distance D when the insert is a single insert in the form of a substantial U-shape, it will be apparent to a person skilled in the art that the same will apply to the largest distance D between separate and oppositely disposed inserts forming plural distinct channels.

In an embodiment, the first, second, third, and/or fourth auxiliary moving surfaces (12, 13, 14, 15) are connected to one or more compression springs and/or dampeners. This has the advantage of absorbing the shocks generated by the rotating inserts as will be described in more detail hereinbelow.

Preferably, the first, second, third, and/or fourth auxiliary moving surfaces (12, 13, 14, 15) comprise an outer abrading surface (16) and a plurality of fanning out spoke-like members (17) that converge towards the rotation axis of said first, second, third, and/or fourth auxiliary moving surfaces (12, 13, 14, 15), preferably wherein the spoke-like members (17) are made of a pliable material comprising, and preferably selected from, polyurethane, more preferably being the same material as the abrading surface (16). Advantageously, this arrangement has been found beneficial to allow for pressure rollers that themselves absorb shocks created by the impacting/rotating inserts at high speed thus allowing to omit expensive and complex spring, dampeners and swing-arm arrangements thus also improving the wear and tear performance of respective components through long production cycles at very high speeds of in excess of 900 pieces per minute.

Preferably, the spoke-like members (17) have a minimum and a maximum thickness, wherein the minimum thickness is proximal to an axis of rotation thereof, and the maximum thickness is proximal to the abrading surface (16) and distal from said axis of rotation. Preferably, a gap (or void) is formed between each consecutive spoke-like members (17) which when seen in the cross-sectional plane perpendicular to the axis of rotation thereof (as illustrated in FIG. 5) said gap(s) (or void(s)) has a substantially triangular shape.

Figure 5:
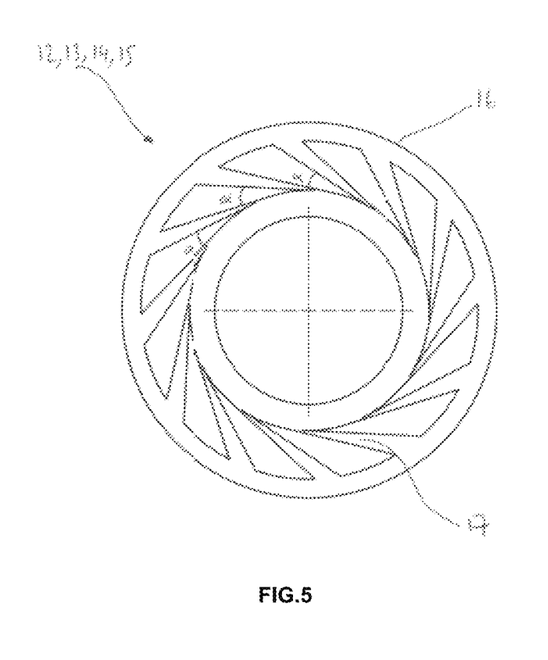
FIG. 5 is a side view illustration of auxiliary endless moving surface(s) according to an embodiment herein.

In a preferred embodiment, as illustrated in FIG. 5, the spoke-like members (17) form an angle ($\alpha$) with respect to each other neighboring spoke-like members (17), typically wherein said angle ($\alpha$) is from 10° to 60°, preferably from 15° to 55°, more preferably from 20° to 45°, even more preferably from 25° to 40°. Advantageously, this arrangement allows for efficiently and effectively allow of shock absorption via buckling effects enabled by the spokes which especially when made of a material selected from polyurethane as described above surprisingly allow for a very resilient and strong structure with sufficient flexibility to deform and return to its original shape upon application of large forces. This has been found to be an additional enabler for eliminating expensive and difficult to maintain mechanical or hydraulic or pneumatic components such as springs and dampeners or the like.

THE PROCESS

Figure 6:
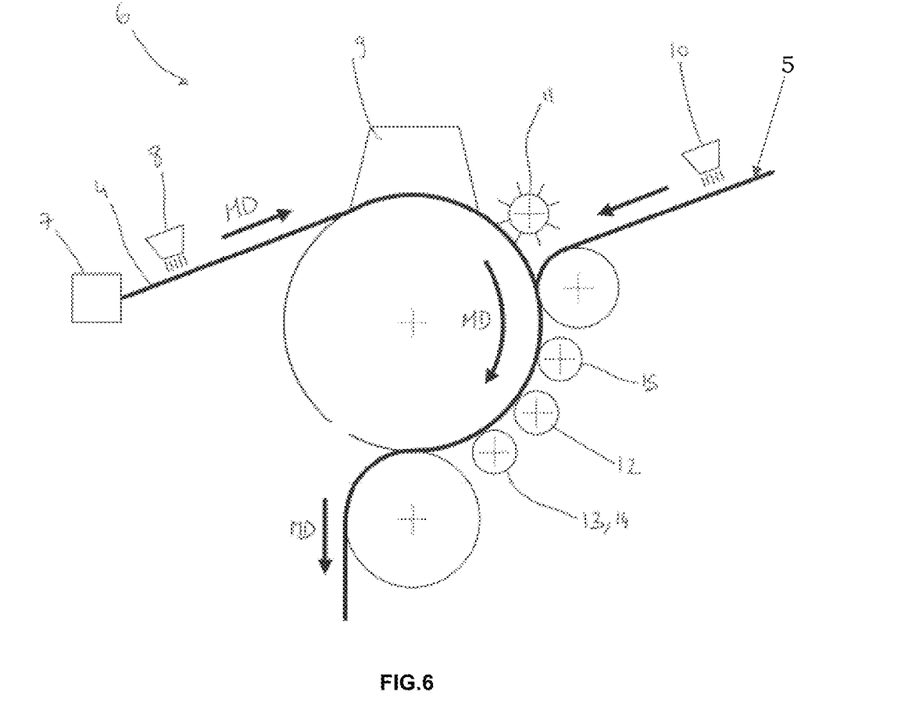
FIG. 6 is a schematic drawing illustrating a process according to an embodiment herein.

The present disclosure further relates to a process or method for making an absorbent core and article, as illustrated in FIG. 6, comprising said core having one or more channels, the method may comprise the steps of: i. providing a first endless moving surface (1) comprising a plurality of molds (2), each mold (2) comprising a non-porous insert (3) therein, typically said insert (3) having the inverse shape of said channel(s), wherein the molds (2) are in fluid communication with an under-pressure source except for said insert (3); ii. feeding a first nonwoven web (4) to said first endless moving surface (1) and over one or more said molds (2); iii. depositing an absorbent material, comprising cellulose fibers and/or superabsorbent polymer particles, over at least a portion of said nonwoven web (4); iv. optionally removing said absorbent material from areas of the nonwoven web (4) corresponding to said insert (3); v. applying a second nonwoven web (5) directly or indirectly over the absorbent material, or folding said first nonwoven web (4), such to sandwich said absorbent material between upper and lower layers (herein also referred to as "core wrap layers or surfaces") of said nonwoven web(s) (4, 5); vi. joining said upper and lower layers together at least in the areas of the nonwoven web(s) (4, 5) corresponding to the insert (3) to form an absorbent core having one or more channels substantially free of absorbent material; vii. optionally joining an acquisition distribution layer to said absorbent core, typically a skin facing surface of said upper layer; viii. optionally laminating said absorbent core and acquisition distribution layer between a liquid pervious topsheet and a liquid impervious backsheet; wherein step vi. comprises the step of selectively applying a first pressure onto the absorbent core, preferably only, in a central portion thereof and a second pressure, preferably only, along peripheral longitudinal side edges thereof running opposite and parallel to each other and being outboard of said central portion, said central portion corresponding at least to a region of the core comprising said channel(s), and wherein said first and second pressures are successively applied along a machine direction (MD).

In an embodiment, the disclosure relates to a method for making an absorbent article comprising an absorbent core comprising one or more channels, the method comprising the steps of: i. providing a first endless moving surface (1) comprising a plurality of molds (2), each mold (2) comprising a non-porous insert (3) therein, typically said insert (3) having the inverse shape of said channel(s), wherein the molds (2) are in fluid communication with an under-pressure source except for said insert (3); ii. feeding a first nonwoven web (4) to said first endless moving surface (1) and over one or more said molds (2); iii. depositing an absorbent material, comprising cellulose fibers and/or superabsorbent polymer particles, over at least a portion of said nonwoven web (4); iv. optionally removing said absorbent material from areas of the nonwoven web (4) corresponding to said insert (3); v. applying a second nonwoven web (5) directly or indirectly over the absorbent material, or folding said first nonwoven web (4), such to sandwich said absorbent material between upper and lower layers of said nonwoven web(s) (4, 5); vi. joining said upper and lower layers together at least in the areas of the nonwoven web(s) corresponding to the insert (3) to form an absorbent core having one or more channels substantially free of absorbent material; vii. optionally joining an acquisition distribution layer to said absorbent core, typically a skin facing surface of said upper layer; viii. optionally laminating said absorbent core and acquisition distribution layer between a liquid pervious topsheet and a liquid impervious backsheet; wherein step vi. comprises the step of selectively applying a first pressure onto the absorbent core, preferably only, in a central portion thereof and a further pressure onto the absorbent core, preferably only, in the central portion thereof, wherein said further pressure is applied upstream of said first pressure and arranged to provide a pre-compression force onto the absorbent core in an area of said core corresponding to said channels.

Preferably, the first pressure is applied upstream of the second pressure. It has been found that by applying pressure to the central portion/region of the absorbent core as early as possible after the marriage point of the top and bottom core wrap layers (or surfaces) a better adhesion of said surfaces is achieved with limited risk of contaminating the channel region with absorbent material that would otherwise reduce the bonding strength between such surfaces and/or lead to damage, such as tearing, of one or more of the core wrap layers. At the same time applying the pressures sequentially at different positions along the machine direction allow for excess air that is entrapped between the core wrap layers to be evacuated from the central portion to the peripheral longitudinal edges (or the opening formed by the fold) and thus aiding to improve core stability compared to simultaneously applying the first and second pressures.

In a preferred embodiment, as illustrated on FIGS. 3-4 and FIG. 5, step vi. comprises the further step of applying a third pressure onto the absorbent core, preferably only, in the central portion thereof, wherein said third pressure is applied upstream of said first pressure, preferably said third pressure arranged to provide a pre-compression force onto the absorbent core in an area of said core corresponding to said channels.

In an embodiment, the third pressure is less than or equal to the first pressure, preferably such that the pre-compression force is less than a force generated by the first pressure onto said absorbent core.

Preferably, the second pressure is greater or equal to the first pressure. Alternatively, the second pressure is less than or equal to the first pressure. In an embodiment, the second pressure is less than or equal to the third pressure.

In an embodiment, the process comprises the step of applying an adhesive pattern onto the acquisition distribution layer or a skin facing surface of the upper layer of the core and laminating said acquisition distribution layer to said absorbent core wherein said adhesive pattern is positioned inboard and/or outboard of the channel(s) such that substantially no adhesive pattern overlaps with said channel (s), and wherein the acquisition distribution layer comprises a spunbond and/or carded, typically thermo carded, nonwoven layer. Advantageously, acquisition distribution layers being selected from spunbond and/or carded nonwovens work synergistically with the channel(s) to provide fast liquid drainage and reduce rewet. Indeed, acquisition distribution layers have evolved from spunbond materials to nowadays more highly performing air-through bonded nonwovens, nevertheless it has been found that when utilizing a channeled core the sponge-like behavior of highly porous air-through bonded nonwovens provides for disadvantages in rewet that outweigh the fluid distribution capabilities that are now for the majority attained by the presence of the channel(s). Moreover, ensuring that no or minimal adhesive is present in the channel region between the core and acquisition distribution layer ensures to minimize drawbacks to effective drainage provided by the channel(s) and thus permitting the use of spunbond and/or carded nonwovens to be used with added overall performance as well as reduced cost.

Preferably, the acquisition distribution layer comprises synthetic fibers, wherein said synthetic fibers are comprised at a level of greater than 80% wt by weight of said acquisition distribution layer, and wherein said acquisition distribution layer has a basis weight of from 10 to 50 g/m², and preferably wherein the acquisition distribution layer is or consists of one or more layers, preferably single-layer, of spunbond or carded, preferably thermo-carded nonwovens.

In a preferred embodiment, the adhesive pattern is in the form of a plurality of stripes or spirals being spaced apart in a transverse axis extending perpendicular to the machine direction.

In an embodiment, step vii comprises the step of applying pressure to the acquisition distribution layer and the absorbent core in the channel(s) such that said acquisition distribution layer is pressed into contact with the upper layer of the nonwoven web(s), preferably wherein said acquisition distribution layer is arranged to be in contact with said upper layer in dry state such to form one or more ditches and to freely displace away from said upper layer in wet state.

The invention claimed is:

1. An apparatus (6) for making an absorbent article comprising an absorbent core comprising one or more channels and sandwiching an absorbent material between a first nonwoven web (4) and a second nonwoven web (5), said apparatus comprising:
a first endless moving surface (1) in the form of a rotating drum, said drum comprising a plurality of molds (2) in the form of pockets successively positioned along a circumference of said drum, wherein each mold (2) comprises a non-porous insert (3) therein, wherein the molds (2) are in fluid communication with an under-pressure source except for said insert (3) such to form one or more non-suction zones corresponding to said non-porous insert (3) and a suction zone surrounding said non-porous insert (3);
a first adhesive application unit (8) for applying an adhesive pattern over a skin-facing surface of said first nonwoven web (4);
an absorbent material deposition unit (9) for depositing an absorbent material over at least a portion of said first nonwoven web (4);
a first auxiliary moving surface (12) for applying a first pressure to the upper and lower layers of said nonwoven web(s) (4, 5);
characterized in that the apparatus (6) further comprises a second and third auxiliary moving surfaces (13, 14) for applying a second pressure to the upper and lower layers of said nonwoven web(s) (4, 5), wherein said first endless moving surface (1), said first auxiliary moving surface (12), said second auxiliary moving surface (13) and said third auxiliary moving surface (14) each have an axis of rotation being substantially parallel to each other, and wherein the first endless moving surface (1) and the auxiliary moving surfaces (12, 13, 14) act upon each other by applying pressure to the upper and lower layers of said nonwoven web(s) (4, 5), and in that said first auxiliary moving surface (12) is arranged to selectively apply said first pressure onto the first endless moving surface (1) only in a central portion thereof and said second and third auxiliary moving surfaces (13, 14) are arranged to selectively apply said second pressure onto the first endless moving surface (1) only along peripheral longitudinal side edges thereof running opposite and parallel to each other and being outboard of said central portion.

2. An apparatus (6) according to claim 1 wherein the second and third auxiliary moving surfaces (13, 14) are positioned downstream of the first auxiliary moving surface (12) along a machine direction (MD).

3. An apparatus (6) according to claim 1 wherein the second and third auxiliary moving surfaces (13,14) are spaced apart at a distance extending parallel to the axis of rotation thereof, and wherein the axis of rotation of said second and third auxiliary surfaces (13, 14) substantially coincide.

4. An apparatus (6) according to claim 3 wherein the second and third auxiliary moving surfaces (13, 14) are rotatably connected by a common housing.

5. An apparatus (6) according to claim 1 further comprising a fourth auxiliary moving surface (15) arranged to provide a third pressure onto the first endless moving surface (1) only in the central portion thereof, wherein said third pressure is applied upstream of said first pressure.

6. An apparatus (6) according to claim 5 wherein the first, second, third, and/or fourth auxiliary moving surfaces (12, 13, 14, 15) comprise a substantially smooth outer surface free of protruding embossing and/or mating members, said outer surface being made of a substantially pliable material.

7. An apparatus (6) according to claim 6, wherein the substantially pliable material is selected from the group consisting of plastic, rubber, and silicone.

8. An apparatus (6) according to claim 6, wherein the substantially pliable material comprises polyurethane.

9. An apparatus (6) according to claim 5 wherein the first, second, third, and/or fourth auxiliary moving surfaces (12, 13, 14, 15) each comprise a rotating pressure roller.

10. An apparatus (6) according to claim 5 wherein the first auxiliary moving surface (12) has a width, extending perpendicular to the machine direction and parallel to the axis of rotation thereof, that is greater than the width of each of the second and third auxiliary moving surfaces (13, 14).

11. An apparatus (6) according to claim 10 wherein the fourth auxiliary moving surface (15) has a width, extending perpendicular to the machine direction and parallel to the axis of rotation, that is greater or equal to the width of the first auxiliary moving surface (12).

12. An apparatus (6) according to claim 5 wherein the first, second, third, and/or fourth auxiliary moving surfaces (12, 13, 14, 15) are connected to one or more compression springs and/or dampeners.

13. An apparatus (6) according to claim 5 wherein the first, second, third, and/or fourth auxiliary moving surfaces (12, 13, 14, 15) comprise an outer abrading surface (16) and a plurality of fanning out spoke-like members (17) that converge towards the rotation axis of said first, second, third, and/or fourth auxiliary moving surfaces (12, 13, 14, 15).

14. An apparatus (6) according to claim 13 wherein the spoke-like members (17) are made of a pliable material comprising polyurethane.

15. An apparatus (6) according to claim 5 wherein said third pressure is arranged to provide a pre-compression force onto the absorbent core, and wherein the third pressure is less than the first pressure, such that the pre-compression force is less than a force generated by the first pressure onto said absorbent core.

16. An apparatus (6) according to claim 1 wherein the second pressure is greater or equal to the first pressure.

* * * * *